United States Patent [19]

Christensen

[11] Patent Number: 4,604,968
[45] Date of Patent: Aug. 12, 1986

[54] INCREASING THE EFFICIENCY OF POULTRY PRODUCTION

[75] Inventor: Vern L. Christensen, Raleigh, N.C.

[73] Assignee: North Carolina State University, Raleigh, N.C.

[21] Appl. No.: 748,165

[22] Filed: Jun. 26, 1985

Related U.S. Application Data

[63] Continuation-in-part of Ser. No. 627,751, Jul. 5, 1984, abandoned.

[51] Int. Cl.$^4$ ............................................. A01K 45/00
[52] U.S. Cl. .......................................................... 119/1
[58] Field of Search ......................... 119/1; 604/49, 51

[56] References Cited

PUBLICATIONS

V. L. Christensen, H. V. Bieller and J. F. Forward, "Physiology of Turkey Embryos During Pipping and Hatching, III. Thyroid Function", 1982 Poultry Science 61:367-374.
R. C. Thommes and V. W. Hykla, "Hypothalamo–Adenohypopyseal–Thyroid Interrelationships in the Chick Embryo, I. TRH and TSH Sensitivity", General and Comparative Endocrinology 34, 193-200 (1978).
V. L. Christensen, H. Biellier, and J. Forward, *Physiology of Turkey Embryos During Pipping and Hatching, II. Selected Blood Parameters*, 1982, Poultry Science 61:143-149.
B. Wentworth, M. Hussein, *Plasma Corticosterone Levels in the Turkey Embryo and the Effects of this Hormone on Hatching*, Abstract 1982 Poultry Science 61:1567.
V. L. Christensen and F. McCorkel, *Turkey Egg Weight Losses and Embryonic Mortality During Incubation*, 1982 Poultry Science 61: 1209-1213.
V. L. Christensen and H. Biellier, *Physiology of Turkey Embryos During Pipping and Hatching, V. Plasma Total Calcium, Magnesium Concentrations, and Total Calcium to Magnesium Ratios,* 1982 Poultry Science 61:1918-1923.
V. L. Christensen and F. McCorkle, *Characterization of Incubational Egg Weight Losses in Three Types of Turkeys,* 1982 Poultry Science 61:848-854.
V. L. Christensen, *Distribution of Pores on Hatching and Nonhatching Turkey Eggs,* 1983 Poultry Science 62: 1312-1316.
V. L. Christensen, C. Parkhurst and F. Edens, *Conductance and Qualities of Wild Domestic Turkey Eggs,* 1982 Poultry Science 61: 1753-1758.
H. Rahn, *Changes in Shell Conductance, Pores and Physical Dimensions of Egg and Shell During the First Breeding Cycle of Turkey Hens,* 1981 Poultry Science 60:2536-2541.
R. Thommes and S. Tonetta, *Hypothalamo–Adenohypophyseal–Thyroid Interrelationships in the Chick Embryo,*
*II. Effects of Thiourea Treatment of Plasma Total Thyroxine Levels and Thyroidal Uptake,* General and Comparative Endocrinology 37, 167-176 (1979).
R. Maraud, M. Aubine and R. Stoll, *Sur l'Existence de Relations Hyophalmo–Hypopysaires, Catz, l'Embryon de Poulet,* Comptes Rendus des Seances de la Societe de Biologie, 169, 923-926.
R. Thommes, R. Vieth and S. Levasseur, *The Effects of Hypophysectomy by Means of Surgical Decapitation on Thyroid Function in the Developing Embryo,* General and Comparative Endocrinology 31, 29-36 (1977).
R. Thommes, J. Martens, W. Hopkins, J. Caliendo, M. Sorrentino and J. Woods *Hypothalamo–Adenohypophyseal–Thyroid Interrelationships in the Chick Embryo, IV. Immunocytochemical Demonstration of TSH in the Hypophyseal Pars Distalis,* General and Comparative Endocrinology 51, 434-443 (1983).
R. Thommes, K. Jameson, *Hypothalamo–Adenohypophyseal–Thyroid Interrelationships in the Chick Embryo, III. Total $T_4$ Levels in the Plasma of Decapitated Chick Embryos with Adenohypopyseal Transplants,* General and Comparative Endocrinology 42, 267,269 (1980).
James Woods, A. Brachmanski and R. Thommes, *Hypothalamo–Adenohypophyseal–Thyroid and Gonadal Interrelationships in the Chick Embryo I. Differential Effect of Ectopic Pituitary Grafts on Plasma Total $T_4$ and Testerone Levels,* General and Comparative Endocrinology 52, 357-364 (1983).
Martin Balaban and Joanna Hill, *Effects of Thyroxine Level and Temperature Manipulations Upon the Hatching of Chick Embryos,* Developmental Psychobiology, 4(1): 17-35 (1971).
G. J. Wishart, J. E. A. Leakey, and G. J. Dutton, *Differential Effects of Hormones on Precocious Yolk Sac Retraction in Chick Embryos Following Administration by a New Technique,* General and Comparative Endocrinology, 31, 373-380 (1977).
M. Borges, J. LaBourene, and S. H. Ingbar, *Changes in Hepatic Iodothyronine Metabolism During Ontogeny of the Chick Embryo,* Endocrinology, vol. 107, No. 6, 1751-1761 (1980).
V. L. Christensen and H. V. Biellier, *Physiology of Turkey Embryos During Pipping and Hatching, IV. Thyroid Function in Embryos from Selected Hens,* 1982 Poultry Science 61:2482-2488.

*Primary Examiner*—Hugh R. Chamblee
*Attorney, Agent, or Firm*—Bell, Seltzer, Park & Gibson

[57] ABSTRACT

The efficiency of poultry production is increased by treating poultry eggs in ovo with physiologic dosages of substances that serve to augment the endogenous thyroid output of the embryos. The disclosed data show improved hatchability rates and a favorable impact on feed conversion rates and mature bird weight.

18 Claims, No Drawings

INCREASING THE EFFICIENCY OF POULTRY PRODUCTION

CROSS REFERENCE TO RELATED APPLICATION

This application is a continuation in part of Ser. No. 627,751, filed July 5, 1984, entitled "Increasing the Hatchability of Poultry Eggs," now abandoned.

BACKGROUND OF THE INVENTION

1. Field of the Invention

The invention relates to the production of poultry, and more particularly to increasing the efficiency of poultry production by acting on hormonal functions of the birds.

2. Description of the Prior Art

The intense genetic selection of turkeys, chickens and other poultry has achieved dramatic increases in body size and growth rates. However, it is well known that genetic selection has adversely affected the efficiency of poultry production by causing alarmingly low average hatchability rates for the eggs, as low as about 70% for many strains of domestic turkeys.

Current efforts to optimize the hatchability of poultry eggs have centered primarily on optimizing the controlled enviromental conditions (e.g. temperature, humidity and gas concentrations) for egg incubation. Other steps, including the injection of antibiotics at different stages of incubation, have been used to control disease.

Looking at domestic turkeys as an example, it is known that over 90% of the embryos of domestic turkeys are alive at or near days 24-25 of incubation, indicating that a very large and significant number of the embryos that do not hatch die late in incubation.

The literature suggests several factors, perhaps interrelated, that may contribute to late embryonic mortality. First, it is known that the eggs breathe totally by gas diffusion through the eggshell (so that the embryo is unable to adjust its gas diffusion rate to coincide with its metabolic rate via increased muscular contraction as mammals, fishes or adult birds do). Therefore, the functional gas conductance properties of the eggshell must be precisely engineered by the hen laying the egg to supply vital gases to an increasing tissue mass. In wild species this delicate balance exists. However, the genetic selection of domestic poultry has caused a dissynchronous relationship between functional eggshell properties and the $O_2$ and $CO_2$ and water vapor requirements of the embryos.

A second observation has been that thyroid hormones play an important physiological role in the successful hatching of domestic poultry. Experimental data have indicated that plasma thyroxine ($T_4$) concentrations appear to be significantly greater at days 26 and 27 of incubation in high hatchability groups of domestic turkey eggs. The high hatchability groups also show significantly higher oxygen consumption, indicating a higher metabolism.

While the above and other phenomena have been suggested by experimental data, prior to this invention there have been no modifications to time honored incubation processes to address the problem of late embryonic mortality.

It is well known that other factors, including feed conversion rates and mature bird weight, have a significant bearing on the overall efficiency of poultry production. The poultry industry has a continuing need for process developments that will optimize these key factors.

SUMMARY OF THE INVENTION

The present invention increases the efficiency of poultry production by providing a dramatic decrease in late embryonic mortality of poultry eggs (and resulting hatchability increases on the order of 6-10% and more) while also having a favorable impact on feed conversion rates and the mature weight of the birds.

Broadly, in one aspect the present invention provides a method of increasing the efficiency of poultry production through treatment of the embryos in ovo during late embryonic development, preferably at or near the onset of pulmonary repiration. The treatment preferably takes the form of an injection of a physiologic dosage of a substance that serves to augment the endogenous thyroid output of the embryo so that the circulating hormone concentrations in hypothyroid, low hatching embryos may be raised to the level found in good hatching embryos.

A preferred substance for injection into poultry eggs in accordance with the invention is thyroid releasing hormone (TRH), a tripeptide pryoglutamyhistidylproline amide released from the hypothalmus. In the treatment of domestic turkey eggs, it has been found that the injection should take place between days 21-26 of incubation, preferably at day 25. With chicken eggs the injection is best made between days 15-18 of incubation, preferably at day 17.

One key advantage of the present invention is that the preferred substances found suitable for injection in accordance with the invention all have been synthesized and are available at reasonable cost. Furthermore, the injection of physiologic dosages, as opposed to pharmacologic dosages, greatly reduces, if not eliminates, the prospect of any adverse impact on the embryo. A further advantage of the invention is that most domestic poultry eggs are injected during late embryonic development with antibiotics to prevent disease. The injection of the present invention may be combined with the antibiotic injection, thus not requiring an additional injection step.

These and other advantages of the invention will become more apparent upon reading of the detailed description which follows.

DETAILED DESCRIPTION OF THE INVENTION

While the present invention will be described more fully hereinafter with reference to certain preferred methods of carrying out the invention, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

The preferred substance for injection into poultry eggs in accordance with the invention is a solution containing thyroid releasing hormone (TRH), a tripeptide pyroglutamyhistidylproline amide released from the hypothalmus as a neuroendocrine thyroid regulator hormone. Other substances that have been tested and have proven effective are:

- thyroxine (T$_4$), a thyroid hormone;
- triiodothyronine (T$_3$), a thyroid hormone;
- thyroid stimulating horomone (TSH; thyrotropin), a neuroendocrine thyroid regulator hormone produced by the pituitary gland; and
- tyrosine, an amino acid precursor of the thyroid hormones, T$_3$ and T$_4$.

Tables I-V below set forth the results of controlled experiments involving each of the substances mentioned above. The experiment for each substance involved two trials with 2,200 eggs per trial. Most of the eggs fell in the weight range of 87-90 grams. Tables I and III-V reflect the average of the two trials for each substance. Because there was a significant statistical difference between the results of trial 1 and trial 2 for the thyroxine (T$_4$) test, the results of both trials are set forth in Table II.

Large White turkey eggs were used from a strain having a usual average hatchability on the order of about 70% of all eggs set. The treatment eggs were injected with an automatic egg injecting machine manufactured by Agrimatic Corp., Paramount, Calif., U.S.A. which is used commercially to inject turkey eggs with antibotics. Other injecting machines or other means for introducing the substances into the eggs, e.g. pressure-immersion techniques, may be used. The term "inject" as used in this specification includes all suitable methods for introducing the injection substance into the egg.

The control eggs were noninjected eggs or, in some instances, sham-injected eggs. There was no significant difference in the hatchability of noninjected vs. sham-injected controls.

The treated eggs were all injected during late embryonic development at the time of transfer of the eggs from the setter to the hatcher at 25 days of incubation, which corresponds approximately to the onset of pulmonary respiration in the embryos.

The percent hatchability was computed by dividing the number of poults hatching per tray by the number of total eggs set on the tray. If eggs were cracked or contaminated, they were omitted from the computations. The hatchability of the fertile eggs was computed by dividing the number of poults hatching per tray by the number of fertile eggs found on the tray.

Injection doses for each of the substances were physiologic, i.e. on the order of the normal level of the substance found in healthy eggs. Thus, the doses were calculated to augment the endogenous thyroid output of the embryos so that the circulating hormone concentrations in hypothyroid, low hatching embryos were raised to the level found in good hatching embryos. All of the synthesized hormones and the synthesized amino acid were supplied by Sigma Chemical Co., St. Louis, Mo., U.S.A. Actual dosages are set forth in the Tables.

TABLE I

Effect of thyroid releasing hormone (TRH) injection on hatchability of turkey eggs.

| Injection Treatment | Hatchability (%) | |
| --- | --- | --- |
| | Of All Eggs | Of Fertile Eggs |
| Treated Dosage - 3.7 ng/egg (0.065 ng/gram of embryo body weight) | 86.5 | 90.7 |
| Control | 74.5 | 78.5 |

TABLE II

Effect of thyroxine (T$_4$) injection on hatchability of turkey eggs

| Trial | Injection Treatment | Hatchability (%) | |
| --- | --- | --- | --- |
| | | Of All Eggs | Of Fertile Eggs |
| 1 | Treatment Dosage 50 ng/egg (0.88 ng/gram of embryo body weight) | 77.8 | 83.1 |
| | Control | 69.7 | 74.0 |
| 2 | Treatment Dosage 50 ng/egg (0.88 ng/gram of embryo body weight) | 75.1 | 79.8 |
| | Control | 69.0 | 73.8 |

TABLE III

Effect of triiodothyronine (T$_3$) injection on hatchability of turkey eggs.

| Injection Treatment | Hatchability (%) | |
| --- | --- | --- |
| | Of All Eggs | Of Fertile Eggs |
| Treatment Dosage - 25 ng/egg (0.44 ng/gram of embryo body weight) | 79.3 | 88.7 |
| Control | 73.4 | 82.3 |

TABLE IV

Effect of thyroid stimulating hormone (TSH) injection on hatchability of turkey eggs.

| Injection Treatment | Hatchability (%) | |
| --- | --- | --- |
| | Of All Eggs | Of Fertile Eggs |
| Treatment Dosage - 1.47 mU/egg (0.026 mU/gram of embryo body weight) | 77.9 | 87.6 |
| Control | 73.9 | 85.9 |

TABLE V

Effect of tyrosine injection on hatchability of turkey eggs

| Injection Treatment | Hatchability (%) | |
| --- | --- | --- |
| | Of All Eggs | Of Fertile Eggs |
| Treatment Dosage - 0.4 mg/egg (0.0071 mg/gram of embryo body weight) | 75.6 | 82.2 |
| Control | 72.0 | 79.0 |

In the injection of domestic turkey eggs it has been found that the injections are best made at day 25 of the 28 day incubation period. However, improved hatchability has been shown by injections made during the late embryonic development period ranging from day 21 to day 26 of incubation.

Referring to the injection of thyroid releasing hormone (Table I), it has been found that the preferred dosage is on the order of about 3.7 nanogram per domestic turkey egg. However, test results indicate that dosages in the range 2.0–10.0 nanogram per domestic turkey egg are satisfactory.

While the tests referred to in the above Tables were all conducted on domestic turkey eggs, the present invention has application to other poultry, for example chickens and ducks. In the case of chickens, the injection should be made at about days 15–18 of incubation, preferably at day 17. In the case of ducks, the injection is best made at about days 21–26 of incubation, preferably at day 25.

The dosages for different poultry are all calculated to achieve a certain increase in circulating hormone levels in the embryos and, therefore, the dosages should vary according to the volume of blood in the embryos of each species. (The volume of blood varies from species to species in approximately the same proportion as the weight varies.) Thus the dosage for chickens (having approximately 75% the embryo body weight of domestic turkeys) should be approximately 75% of that administered to the domestic turkey embryos. Likewise, since domestic duck eggs are about the same size as domestic turkey eggs, the same dosages may be used.

In addition to setting forth the precise dosages injected into the turkey eggs during the tests, Tables I–V also set forth the preferred dosage/body weight figures for each of the five injected substances.

While not reflected by the Tables or the above discussion, the injection may include a combination of two or more substances, preferably both in physiologic dosages that may be somewhat smaller than those specified above.

The injection treatment of turkey eggs referred to in Table I (i.e. the in ovo injection of TRH at day 25 at a dosage of approximately 4 ng/egg) was repeated and the feed conversion and growth rates of the birds were followed from hatching until market age of the birds—week 15 for hens and week 18 for toms. It was found that the average weight of the market age hens increased on the order of 2.5 to 5 points (+0.25 to +0.50 lb.) and that the average feed conversion rate showed a favorable decrease on the order of 10 points (each unit of weight gain required 0.10 less units of feed). The average weight of the market age toms increased on the order of 3 to 4 points, while the average feed conversion rate for toms was not materially affected. The cumulative mortality of the birds was also observed and the injections produced no significant effect on hens and an increase in toms. All comparisons are to noninjected control groups.

It will be understood that modifications may be made to the above methods without departing from the true spirit and scope of the invention. For example, analogs to the disclosed injection substances may be used where efficacious.

What is claimed is:

1. A method of increasing the efficiency of poultry production comprising injecting poultry eggs during late embryonic development with a substance that operates to augment the endogenous thyroid output of the embryos, said substance being injected at a time and in an amount effective to increase the efficiency of poultry production as measured by a favorable impact on at least one of the following: (i) hatchability rate, (ii) feed conversion rate, (iii) mature bird weight and (iv) mortality rate.

2. The method of claim 1 wherein the type of poultry is domestic turkeys or domestic ducks and the injecting step is carried out at day 21 to 26 of incubation.

3. The method of claim 2 wherein the injecting step is carried out at day 25 of incubation.

4. The method of claim 1 wherein the type of poultry is chickens and the injecting step is carried out at day 15 to 18 of incubation.

5. The method of claim 4 wherein the injecting step is carried out at day 17 of incubation.

6. A method of increasing the efficiency of poultry production comprising injecting poultry eggs at or near the onset of pulmonary respiration with a physiologic dosage of a thyroid hormone, a thyroid hormone precursor or a neuroendocrine thyroid regulator hormone, said physiologic dosage being on the order of the normal level of the substance found in healthy eggs.

7. The method of claim 6 wherein the injection includes thyroid releasing hormone (TRH) at a dosage on the order of about 0.065 nanogram TRH per gram of embryo body weight.

8. The method of claim 6 wherein the injection includes thyroxine ($T_4$) at a dosage on the order of about 0.88 nanogram $T_4$ per gram of embryo body weight.

9. The method of claim 6 wherein the injection includes triiodothyronine ($T_3$) at a dosage on the order of about 0.44 nanogram $T_3$ per gram of embryo body weight.

10. The method of claim 6 wherein the injection includes thyroid stimulating hormone (TSH) at a dosage on the order of about 0.026 mU TSH per gram of embryo body weight.

11. A method of increasing the efficiency of domestic turkey production comprising injecting turkey eggs at day 21 to 26 of incubation with a solution containing thyroid release hormone (TRH) at a dosage on the order of 2.0–10.0 nanogram TRH per egg.

12. The method of claim 11 wherein the dosage is on the order of about 3.7 nanogram TRH per egg.

13. The method of claim 11 wherein the step of injecting the eggs is carried out at day 25 of incubation.

14. The method of claim 12 wherein the step of injecting the eggs is carried out at day 25 of incubation.

15. A method of increasing the efficiency of poultry production comprising injecting poultry eggs during late embryonic development with a compound selected from the class consisting of thyroid releasing hormone, thyroxine, triiodothyronine, thyroid stimulating hormone and tyrosine, said compound being injected at a time and in an amount effective to substantially reduce the probability of late embryonic mortality for the embryo being treated.

16. A method of increasing the hatchability of poultry eggs comprising injecting the eggs during late embryonic development with a substance that operates to augment the endogenous thyroid output of the embryos, said substance being injected at a time and in an amount effective to increase the hatchability rate of the eggs.

17. The method of claim 16 wherein the type of poultry is domestic turkeys or domestic ducks and the injecting step is carried out on or about day 25 of incubation.

18. The method of claim 16 wherein the type of poultry is chickens and the injecting step is carried out on or about day 17 of incubation.

* * * * *